United States Patent [19]

Barnes et al.

[11] 4,291,033
[45] Sep. 22, 1981

[54] OXOIMIDAZOQUINOXALINES

[75] Inventors: Alan C. Barnes, Cirencester; David P. Kay, Swindon, both of Great Britain

[73] Assignee: Roussel Uclaf, Paris, France

[21] Appl. No.: 118,522

[22] Filed: Feb. 4, 1980

[30] Foreign Application Priority Data

Feb. 9, 1979 [GB] United Kingdom ............... 04648/79
Jun. 7, 1979 [GB] United Kingdom ............... 19847/79

[51] Int. Cl.³ .................. C07D 487/04; A61K 31/495
[52] U.S. Cl. ............................. 424/250; 424/248.53; 424/248.55; 544/64; 544/115; 544/225; 544/346
[58] Field of Search ...................... 544/346, 225, 115; 424/250

[56] References Cited

U.S. PATENT DOCUMENTS

| | | | |
|---|---|---|---|
| 3,887,566 | 6/1975 | Rodway et al. | 544/346 |
| 3,994,893 | 11/1976 | Treuner | 544/346 |
| 4,075,343 | 2/1978 | Kadin | 424/258 |
| 4,145,419 | 3/1979 | Rowlands et al. | 424/248.4 |
| 4,151,280 | 4/1979 | Rowlands et al. | 424/250 |
| 4,207,318 | 6/1980 | Rowlands et al. | 424/248.4 |

*Primary Examiner*—Donald G. Daus
*Assistant Examiner*—James H. Turnipseed
*Attorney, Agent, or Firm*—Hammond & Littell, Weissenberger and Muserlian

[57] ABSTRACT

Novel oxoimidazoquinoxalines of the formula

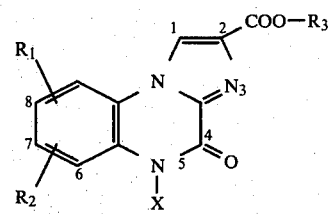

wherein $R_1$ and $R_2$ are individually selected from the group consisting of hydrogen, chlorine and bromine, X is selected from the group consisting of hydrogen, alkyl of 1 to 5 carbon atoms, cycloalkyl of 3 to 5 carbon atoms and cycloalkyl-alkyl of 4 to 6 carbon atoms, $R_3$ is selected from the group consisting of hydrogen alkyl of 1 to 5 carbon atoms, alkali metal, alkaline earth metal, aluminum, $-NH_4$, organic amine and

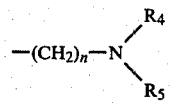

$R_4$ and $R_5$ are individually alkyl of 1 to 5 carbon atoms or taken together with the nitrogen atom form a saturated heterocycle of 4 to 6 carbon atoms optionally containing an oxygen atom or second nitrogen atom and n is a number from 1 to 5 and their non-toxic, pharmaceutically acceptable acid addition salts having antiallergic activity and their preparation.

15 Claims, No Drawings

OXOIMIDAZOQUINOXALINES

STATE OF THE ART

Related compounds are described in U.S. Pat. No. 4,075,343, No. 4,151,280 and No. 4,145,419 and copending, commonly assigned U.S. patent applications Ser. No. 61,626 filed July 30, 1979, No. 958,561 filed Nov. 7, 1978, now U.S. Pat. No. 4,207,318 and No. 869,842 filed Jan. 16, 1978.

OBJECTS OF THE INVENTION

It is an object of the invention to provide a novel oxoimidazoquinoxalines of formula I and novel process for their preparation.

It is a further object of the invention to provide antiallergic compositions and a method of relieving allergic symptoms in warm-blooded animals.

These and other objects and advantages will become obvious from the following detailed description.

THE INVENTION

The novel compounds of the invention are selected from the group consisting of oxoimidazoquinoxalines of the formula

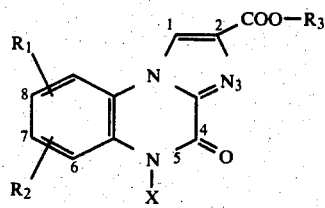

wherein $R_1$ and $R_2$ are individually selected from the group consisting of hydrogen, chlorine and bromine, X is selected from the group consisting of hydrogen, alkyl of 1 to 5 carbon atoms, cycloalkyl of 3 to 5 carbon atoms and cycloalkyl-alkyl of 4 to 6 carbon atoms, $R_3$ is selected from the group consisting of hydrogen, alkyl of 1 to 5 carbon atoms, alkali metal, alkaline earth metal, aluminum, $-NH_4$, organic amine and

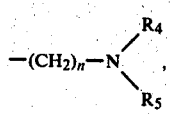

$R_4$ and $R_5$ are individually alkyl of 1 to 5 carbon atoms or taken together with the nitrogen atom form a saturated heterocycle of 4 to 6 carbon atoms optionally containing an oxygen atom or second nitrogen atom and n is a number from 1 to 5 and their non-toxic, pharmaceutically acceptable acid addition salts.

$R_1$ and $R_2$ are preferably in the 7- and 8-positions of the imidazoquinoxaline ring when one or both are a halogen. Examples of alkyl of 1 to 5 carbon atoms are methyl, ethyl, propyl, isopropyl, butyl, isobutyl, pentyl and isopentyl and examples of cycloalkyl of 3 to 5 carbon atoms are cyclopropyl, cyclobutyl and cyclopentyl. An example of cycloalkylalkyl of 4 to 6 carbon atoms is cyclopropylmethyl. Examples of heterocycles of

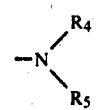

are pyrrolidino, piperidino, morpholino and piperazinyl.

Examples of suitable acids to form the non-toxic, pharmaceutically acceptable acid addition salts are inorganic acids such as hydrochloric acid, hydrobromic acid, hydroiodic acid, nitric acid, phosphoric acid and sulfuric acid and organic acids such as acetic acid, formic acid, propionic acid, benzoic acid and other aryl carboxylic acids, maleic acid, fumaric acid, succinic acid, tartaric acid, citric acid, oxalic acid, glyoxylic, aspartic acid, alkane-sulfonic acids such as methanesulfonic acid or ethanesulfonic acid, arylsulfonic acids such as benzenesulfonic acid and p-toluenesulfonic acid.

Examples of the salts of formula I are alkali metals such as sodium, potassium and lithium, alkaline earth metals such as calcium, or magnesium, aluminum, ammonium and non-toxic, pharmaceutically acceptable organic amines such as lysine, triethanolamine, arginine and tris(hydroxymethyl)-aminomethane.

Among the preferred compounds of the invention are those wherein $R_3$ is hydrogen or ethyl and those wherein $R_1$ and $R_2$ are both hydrogen. Specific preferred compounds of the invention are 4,5-dihydro-5-ethyl-4-oxoimidazo-[1,2-a]-quinoxaline-2-carboxylic acid and 4,5-dihydro-5-propyl-4-oxoimidazo-[1,2-a]-quinoxaline-2-carboxylic acid and their salts.

The compounds of formula I wherein $R_3$ is alkyl of 1 to 5 carbon atoms may be prepared by cyclization of a compound of the formula

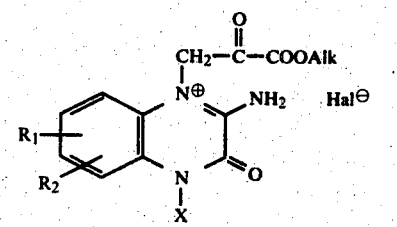

wherein X, $R_1$ and $R_2$ have the above definitions, Hal is chlorine or bromine and Alk is alkyl of 1 to 5 carbon atoms, preferably by heating to reflux, especially in the presence of an alkanol solvent such as ethanol.

The compounds of formula I wherein $R_3$ is alkyl of 1 to 5 carbon atoms and X is hydrogen may be prepared by cyclization of a compound of the formula

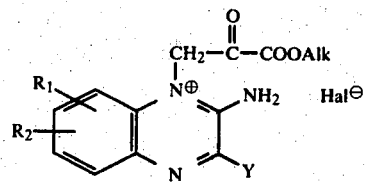

wherein $R_1$, $R_2$, Hal and Alk have the above definitions and Y is bromine or chlorine, preferably by heating at reflux, especially in the presence of an alkanol solvent such as ethanol.

The compounds of formula I wherein X is hydrogen and R₃ is hydrogen or alkyl of 1 to 5 carbon atoms may be prepared by hydrolysis of a compound of the formula

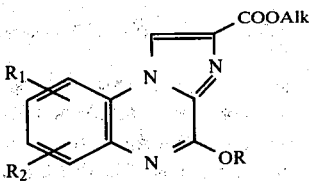    IV wherein R₁, R₂ and Alk have the above definitions and R is alkyl of 1 to 3 carbon atoms. When it is desired to obtain a compound of formula I wherein R₃ is hydrogen, then the hydrolysis is preferably effected under alkaline conditions, for example with an alkali metal hydroxide such as sodium or potassium hydroxide. When it is desired to prepare a compound of formula I wherein R₃ is alkyl of 1 to 5 carbon atoms i.e. to selectively hydrolyze the compound of formula IV, the hydrolysis is preferably effected with an acid, most preferably a dilute acid.

For the preparation of compounds of formula I wherein R₃ is hydrogen, a compound of formula I wherein R₃ is alkyl of 1 to 5 carbon atoms is preferably hydrolyzed under alkaline conditions, for example with an alkali metal hydroxide such as sodium or potassium hydroxide.

For the preparation of compounds of formula I wherein R₃ is alkyl of 1 to 5 carbon atoms or

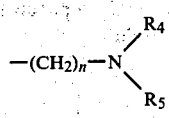

wherein n, R₄ and R₅ have the above definitions, a compound of formula I wherein R₃ is hydrogen or a functional derivative thereof e.g. an acid halide, salt, imidate, anhydride or mixed anhydride is reacted with a compound of the formula

R₃'-OH    V wherein R₃' is alkyl of 1 to 5 carbon atoms or a group of the formula

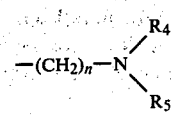

or a functional derivative thereof such as, for example a halide, e.g. a bromide. Thus, for example, a salt e.g. the silver salt of the acid of formula I may be reacted with a functional derivative of the alcohol of formula V e.g. a halide. Alternatively, if desired, the alcohol of formula V may be reacted directly with the acid of formula I or a functional derivative thereof.

For the preparation of compounds of formula I wherein X is alkyl of 1 to 5 carbon atoms, cycloalkyl or cycloalkyl-alkyl radical and R₃ is alkyl of 1 to 5 carbon atoms or a group of the formula

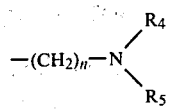

as hereinbefore defined, a compound of formula I wherein X is hydrogen is reacted with a compound of the formula

Z—X'    IV wherein X' is alkyl of 1 to 5 carbon atoms, cycloalkyl or cycloalkyl-alkyl radical and Z is a halogen, e.g. a chlorine, bromine or preferably an iodine atom. The reaction is preferably effected in the presence of a base such as sodium hydride.

The compounds of formula I may, if desired, be converted into their salts e.g. those mentioned above by methods well known in the art, for example by reaction with an appropriate acid or base, preferably in substantially equimolar quantities.

The compounds of formula II useful as starting materials may, for example, be obtained by reaction of a compound of the formula Hal—CH₂—CO—COOAlk    VII wherein Alk and Hal are as defined above with a compound of the formula

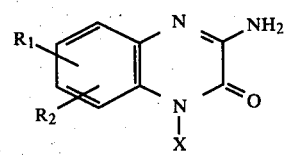    VIII wherein R₁, R₂ and X are as defined above, preferably in the presence of an organic solvent such as, for example, dimethoxyethane or tetrahydrofuran.

Similarly, the compounds of formula III may be obtained, if desired, by reaction of a compound of formula VII with a compound of the formula

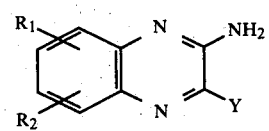    IX wherein Y, R₁ and R₂ are as defined above, again preferably in the presence of an organic solvent such as, for example, dimethoxyethane or tetrahydrofuran.

The compounds of formula IV may be obtained, if desired, by reaction of a compound of formula VII with a compound of the formula

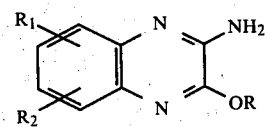    X wherein R₁, R₂ and R are as defined above also preferably in the presence of an organic solvent such as, for example, dimethoxyethane or tetrahydrofuran.

The compounds of formula IX wherein $R_1$ and $R_2$ each represents hydrogen and Y is a chlorine atom may be prepared according to the method of Saikachi and Tagami [Chem. Parm. Bull. Tokyo, (1961) Vol. 9, P. 94] by heating ammonia and 2,3-dichloroquinoxaline together under pressure in the presence of an alkanol e.g. an alkanol of 1 to 3 carbon atoms such as ethanol. 2,3-dichloroquinoxaline may be obtained by reacting phosphorus pentachloride with quinoxaline-2,3-diol by the method of Stevens et al [J.A.C.S. (1946) Vol. 68, p, 1035]. The corresponding compounds in which one or both of $R_1$ and $R_2$ represent halogen atoms and/or Y represents a bromine atom may be made by the same methods.

The compounds of formula X wherein $R_1$ and $R_2$ each is a halogen, one being in the 6 position and the other in the 7 position of the quinoxaline ring, may be obtained by reaction of a 6,7-dihalo-2,3-dichloroquinoxaline with gaseous ammonia at about 0° C. in the presence of an alkanol of 1 to 3 carbon atoms e.g. ethanol and under pressure e.g. in a Cook hydrogenator. The 6,7-dihalo-2,3-dichloroquinoxaline may be obtained by the action of phosphorus pentachloride on a 6,7-dihaloquinoxaline-2,3-diol. 6,7-dichloroquinoxaline-2,3-diol may be prepared by the method of Cheeseman [J.C.S., (1962), P. 1174] i.e. by the reaction of 4,5-dichloro-o-phenylenediamine with diethyl oxalate. The above methods may also be used to make compounds of formula X in which $R_1$ and $R_2$ are both hydrogen or represent one or two halogens in other than the 6 and 7 positions. 6,7-dibromoquinoxaline-2,3-diol may also be prepared according to a method described by Cheeseman [J.C.S., (1962), P. 1170] i.e. by bromination of quinoxaline-2,3-diol in the presence of dimethylaniline.

2,3-dichloroquinoxaline having a single halogen in the aromatic ring or two halogens in other than the 6,7- and 5,8-positions are asymmetrical and on reaction with ammonia in the presence of an alkanol, will give a mixture of two isomeric compounds of formulae IX or X. These mixed isomers may be separated at that stage, for example by chromatography, or may be reacted as a mixture, the separation then being effected at a later stage, for example on esters of formula I in which $R_3$ is an alkyl of 1 to 5 carbon atoms.

The antiallergic compositions of the invention are comprised of an antiallergically effective amount of at least one oxoimidazoquinoxaline of formula I and their non-toxic, pharmaceutically acceptable acid addition salts and an inert pharmaceutical carrier or excipient. The compositions may be in the form of tablets, coated tablets, gelatin capsules, aerosols, granules, syrups, creams, ointments, suppositories and solutions and suspensions for injection.

The active ingredient may be incorporated in excipients customarily employed in pharmaceutical compositions such as, for example, talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Because of their antiallergic activity the compositions are useful in the treatment of asthma and bronchial asthma of allergic origins.

The novel method of the invention for relieving allergic symptoms in warm-blooded animals, including humans, comprises administering to warm-blooded animals an anti-allergically effective amount of at least one compound of formula I and its non-toxic, pharmaceutically acceptable acid addition salts. The active compound may be administered orally, rectally, parenterally or topically. The usual daily dose is 0.005 to 2 mg/kg depending on the compound and the method of administration.

In the following examples there are described several preferred embodiments to illustrate the invention. However, it is to be understood that the invention is not intended to be limited to the specific embodiments.

EXAMPLE 1

Ethyl 4,5-dihydro-4-oxoimidazo-[1,2-a]-quinoxaline-2-carboxylate

STEP A:
2-amino-1-carbethoxycarbonylmethyl-3-chloroquinoxalinium bromide

A solution of 9 g of 2-amino-3-chloro-quinoxaline [prepared by heating under pressure in ethanol, ammonia and 2,3-dichlorquinoxaline as taught by Saikachi et al (Chem. Pharm. Bull. Tokyo (1961), Vol. 9, P. 94)], 12 g of ethyl bromopyruvate and 180 ml of dimethoxyethane was stirred overnight and was then vacuum filtered to recover 5.33 g of a pale yellow crystalline solid. The filtrate stood in the refrigerator for several days to recover 1.20g and 3.62 g of the same compound for a total yield of 10.22 g of 2-amino-1-carbethoxycarbonylmethyl-3-chloro-quinoxalinium bromide.

STEP B: Ethyl 4,5-dihydro-4-oxoimidazo-[1,2-a]-quinoxaline-2-carboxylate

A suspension of 6.5 g of the product of Step A in 500 ml of ethanol was refluxed with stirring for 2 hours and the resulting clear yellow solution was concentrated and cooled in a refrigerator. The mixture was filtered and then 3.70 g of white crystalline product was crystallized from ethanol to obtain ethyl 4,5-dihydro-4-oxoimidazo-[1,2-a]-quinoxaline-2-carboxylate in the form of shiny crystals melting at 292°-293° C.

Analysis: $C_{13}H_{11}N_3O_3$; molecular weight=257. Calculated: %C, 60.70; %H, 4.31; %N, 16.33. Found: %C, 60.50; %H, 4.33; %N, 16.36.

The 2,3-dichloroquinoxaline was prepared by reacting quinoxaline-2,3-diol and phosphorus pentachloride by the method of Stevens et al [J.A.C.S., Vol. 68 (1946), P. 1035].

EXAMPLE 2

4,5-dihydro-4-oxoimidazo-[1,2-a]-quinoxaline-2-carboxylic acid

A suspension of 0.5 g of the product of Example 1, 50 ml of water, 15 ml of ethanol and 8 ml of 1 N sodium hydroxide solution was stirred overnight and the resulting colorless solution was acidified with concentrated hydrochloric acid. The mixture was filtered to obtain 0.44 g of 4,5-dihydro-4-oxoimidazo-[1,2-a]-quinoxaline-2-carboxylic acid in the form of a white crystalline solid melting at 272°-275° C. with decomposition.

Analysis: $C_{11}H_7N_3O_3\text{-}\frac{1}{4}$ $H_2O$; molecular weight=235. Calculated: %C, 56.53; %H, 3.24; %N, 17.98. Found: %C, 56.59; %H, 3.24; %N, 18.03.

EXAMPLE 3

Ethyl 4,5-dihydro-5-methyl-4-oxoimidazo-[1,2-a]-quinoxaline-2-carboxylate 0.1 g of sodium hydride as an 80% oil dispersion was added to a solution of 0.7 g of the product of Example 1 in 30 ml of dimethylformamide and the solution was stirred for 10 minutes whereby a gelatinous precipitate of a sodium salt formed. 0.6 g of methyl iodide were added to the mixture which was then stirred overnight and the resulting clear yellow solution was poured into ice. The mixture was filtered to obtain 0.5 g of ethyl 4,5-dihydro-5-methyl-4-oxoimidazo-[1,2a]-quinoxaline-2-carboxylate as a soft white solid which when crystallized from ethanol yielded soft white needles melting at 220° C.

Analysis: $C_{14}H_{13}N_3O_3$; molecular weight=271. Calculated: %C, 61.99; %H, 4.83; %N, 15.49. Found: %C, 61.90; %H, 4.82; %N, 15.50.

EXAMPLE 4

4,5-dihydro-5-methyl-4-oxoimidazo-[1,2-a]-quinoxaline-2-carboxylic acid

The product of Example 3 was hydrolyzed by the procedure of Example 2 to obtain a 100% yield of 4,5-dihydro-5-methyl-4-oxoimidazo-[1,2-a]-quinoxaline-2-carboxylic acid melting at 267°–268° C.

Analysis: $C_{12}H_9N_3O_3 \cdot \frac{1}{2} H_2O$; molecular weight=252. Calculated: %C, 57.13; %H, 3.99; %N, 16.66. Found: %C, 57.72; %H, 3.98; %N, 16.77.

EXAMPLE 5

Ethyl 4,5-dihydro-5-ethyl-4-oxoimidazo-[1,2-a]-quinoxaline-2-carboxylate

The procedure of Example 3 was repeated using ethyl iodide with 3 hours of stirring after its addition. When the reaction mixture was stirred overnight, two products were formed, namely the N-ethyl and O-ethyl derivatives. The products were separated by column chromatography over silica gel with the non-polar O-ethyl derivative eluted first with ethyl acetate having a melting point of 191°–194° C., Ethyl-4,5-dihydro-5-ethyl-4-oxoimidazo-[1,2-a]-quinoxaline-2-carboxylate was obtained in a 63% yield and it occurred in the form of white shiny micro needles melting at 216°–218° C. after crystallization from ethanol.

Analysis: $C_{15}H_{15}N_3O_3$; molecular weight=285. Calculated: %C, 63.15; %H, 5.30; %N, 14.73. Found: %C, 63.06; %H, 5.26; %N, 14.78.

EXAMPLE 6

4,5-dihydro-5-ethyl-4-oxoimidazo-[1,2-a]-quinoxaline-2-carboxylic acid

The product of Example 5 was hydrolyzed by the process of Example 2 to obtain a 79% yield of 4,5-dihydro-5-ethyl-4-oxoimidazo-[1,2-a]-quinoxaline-2-carboxylic acid melting at 250°–252° C.

Analysis: $C_{13}H_{11}N_3O_3$; molecular weight=257. Calculated: %C, 60.70; %H, 4.31; %N, 16.33. Found: %C, 60.59; %H, 4.29; %N, 16.29.

EXAMPLE 7

Ethyl 4,5-dihydro-5-propyl-4-oxoimidazo-[1,2-a]-quinoxaline-2-carboxylate

The procedure of Example 3 was carried out with n-propyl iodide and stirring for 3 hours to obtain a 64.5% yield of ethyl 4,5-dihydro-5-propyl-4-oxoimidazo-[1,2-a]-quinoxaline-2-carboxylate in the form of white needles melting at 212°–214° C. after crystallization from ethanol.

Analysis: $C_{16}H_{17}N_3O_3$; molecular weight=299. Calculated: %C, 64.20; %H, 5.72; %N, 14.04. Found: %C, 64.22; %H, 5.69; %N, 14.13.

EXAMPLE 8

4,5-dihydro-5-propyl-4-oxoimidazo-[1,2-a]-quinoxaline-2-carboxylic acid

The product of Example 7 was hydrolyzed by the procedure of Example 2 to obtain a 100% yield of 4,5-dihydro-5-propyl-4-oxoimidazo-[1,2-a]-quinoxaline-2-carboxylic acid melting at 232°–234° C.

Analysis: $C_{14}H_{13}N_3O_3 \cdot H_2O$; molecular weight=289. Calculated: %C, 58.13; %H, 5.23; %N, 14.53. Found: %C, 57.89; %H, 5.18; %N, 14.52.

EXAMPLE 9

Ethyl 4,5-dihydro-5-butyl-4-oxoimidazo-[1,2-a]-quinoxaline-2-carboxylate

The procedure of Example 3 was repeated with n-butyl iodide and the product was chromatographed over silica gel. Elution with ethyl acetate gave a 43% yield of ethyl 4,5-dihydro-5-butyl-4-oxoimidazo-[1,2-a]-quinoxaline-2-carboxylate melting at 205°–209° C.

Analysis: $C_{17}H_{19}N_3O_3$; molecular weight=313. Calculated: %C, 65.16; %H, 6.11; %N, 13.41. Found: %C, 65.04; %H, 6.04; %N, 13.38.

EXAMPLE 10

4,5-dihydro-5-butyl-4-oxoimidazo-[1,2-a]-quinoxaline-2-carboxylic acid

The product of Example 9 was hydrolyzed by the procedure of Example 2 to obtain a 100% yield of 4,5-dihydro-5-butyl-4-oxoimidazo-[1,2-a]-quinoxaline-2-carboxylic acid melting at 220°–222° C.

Analysis: $C_{15}H_{15}N_3O_3 \cdot H_2O$; molecular weight=303. Calculated: %C 59.40; %H, 5.65; %N, 13.85. Found: %C, 59.40; %H, 5.52; %N, 13.85.

EXAMPLE 11

7,8-dichloro-4,5-dihydro-4-oxoimidazo-[1,2-a]-quinoxaline-2-carboxylic acid

STEP A: 2-amino-6,7-dichloro-3-ethoxy-quinoxaline 4,5-dichloro-o-phenylenediamine and diethyl oxalate were reacted by the procedure of Cheeseman [J.C.S., (1962), p. 1174] to obtain 6,7-dichloroquinoxaline-2,3-diol which was reacted with phosphorus oxychloride/phosphorus pentachloride to form 2,3,6,7-tetrachloroquinoxaline.

A solution of 3.46 g of 2,3,6,7-tetrachloroquinoxaline in 200 ml of ethanol was saturated with ammonia at 0° C. and was then shaken overnight at 80° C. under pressure in a Cook Hydrogenator. The solution was evaporated to dryness and the residue was triturated with water to obtain a buff crystalline solid. The latter was chromatographed over silica gel and was eluted with a 1-1 ethyl acetate-petroleum ether (b.p.=60° to 80° C.) mixture to obtain 1.36 g of 2-amino-6,7-dichloro-3-ethoxy-quinoxaline melting at 191°-193° C.

STEP B: Ethyl 4-ethoxy-7,8-dichloroimidazo-[1,2-a]-quinoxaline-2-carboxylate A solution of 1 g of the product of Step A, 1 g of ethyl bromopyruvate and 50 ml of dimethylethane was stirred at room temperature for 5 days and the mixture was filtered to recover 0.51 g of a white crystalline solid. The latter was chromatographed over silica gel and was eluted with chloroform to obtain 0.15 g of ethyl 4-ethoxy-7,8-dichloroimidazo-[1,2-a]-quinoxaline-2-carboxylate in the form of a white crystalline solid melting at 256°-258° C.

STEP C: 4,5-dihydro-7,8-dichloro-4-oxoimidazo-[1,2-a]-quinoxaline-2-carboxylic acid A mixture of 0.14 g of the product of Step B, 10 ml of ethanol, 20 ml of water and 3 ml of 1 N sodium hydroxide solution was refluxed overnight and the resulting clear solution was acidified with concentrated hydrochloric acid. The mixture was filtered to obtain 0.12 g of 4,5-dihydro-7,8-dichloro-4-oxoimidazo-[1,2-a]-quinoxaline-2-carboxylic acid in the form of a white crystalline solid.

Analysis: $C_{11}H_5N_3O_3Cl_2 \cdot H_2O$; molecular weight=316. Calculated: %C, 41.80; %H, 2.23; %N, 13.30. Found: %C, 42.35; %H, 2.26; %N, 13.40.

EXAMPLE 12

4,5-dihydro-7,8-dibromo-4-oxoimidazo-[1,2-a]-quinoxaline-2-carboxylic acid

STEP A: 2-amino-6,7-dibromo-3-ethoxy-quinoxaline

Quinoxaline-2,3-diol was brominated to form 6,7-dibromo-quinoxaline-2,3-diol which was then reacted with phosphorus oxychloride to the presence of dimethyl aniline by the procedure of Cheeseman [J.C.S., (1962), P. 1170] to form 6,7-dibromo-2,3-dichloroquinoxaline. The latter compound was reacted as in Step A of Example 11 to obtain 2-amino-6,7-dibromo-3-ethoxy-quinoxaline.

STEP B: 2-amino-6,7-dibromo-1-carbethoxycarbonylmethyl-3-ethoxy-quinoxalinium bromide A solution of 0.68 g of the product of Step A in 25 ml of dimethoxyethane and 0.5 g of ethyl bromopyruvate was stirred for 5 days at room temperature and the mixture was filtered to obtain 0.6 g of 2-amino-6,7-dibromo-1-carbethoxycarbonylmethyl-3-ethoxy-quinoxalinium bromide as a white crystalline solid.

STEP C: Ethyl 7,8-dibromo-4-ethoxy-imidazo-[1,2-a]-quinoxaline-2-carboxylate A suspension of 0.5 g of the product of Step B in 50 ml of ethanol was refluxed for 3 hours and the resulting clear, colorless solution was concentrated and cooled. The mixture was filtered to obtain 0.35 g of a white crystalline solid which was chromatographed over silica gel. Elution with a 1-1 ethyl acetate-petroleum ether (b.p.=60° to 80° C.) mixture yielded ethyl 7,8-dibromo-4-ethoxy-imidazo-[1,2-a]-quinoxaline-2-carboxylate which melted at 247°-249° C. after crystallization from an ethanol-ethyl acetate mixture.

Analysis: $C_{15}H_{13}N_3O_3Br_2$; molecular weight=443. Calculated: %C, 40.66; %H, 2.96; %N, 9.48. Found: %C, 40.52; %H, 2.96; %N, 9.42.

STEP D: 4,5-dihydro-7,8-dibromo-4-oxoimidazo-[1,2-a]-quinoxaline-2-carboxylic acid A suspension of 0.1 g of the product of Step C, 10 ml of ethanol, 20 ml of water and 3 ml of 1 N sodium hydroxide solution was refluxed overnight and the resulting clear solution was acidified with concentrated hydrochloric acid. The mixture was filtered to obtain 0.053 g of 4,5-dihydro-7,8-dibromo-4-oxoimidazo-[1,2-a]-quinoxaline-2-carboxylic acid as a buff crystalline solid.

IR Spectrum (KBr): $\nu$OH at 3420 cm$^{-1}$ (acid OH); $\nu$NH at 3200 cm$^{-1}$ (amide); $\nu$CH at 3110 cm$^{-1}$ (imidazole CH); and $\nu$CO at 1705 cm$^{-1}$ (acid+amide carbonyls).

EXAMPLE 13

Tablets were prepared containing 2 mg of 4,5-dihydro-5-ethyl-4-oxoimidazo-[1,2-a]-quinoxaline-2-carboxylic acid or 5 mg of 4,5-dihydro-5-propyl-4-oxoimidazo-[1,2-a]-quinoxaline-2-carboxylic acid and sufficient excipient of lactose, starch, talc and magnesium stearate to obtain a final weight of 100 mg.

Dosed aerosols were prepared so that each delivered dose consisted of 2 mg of 4,5-dihydro-5-ethyl-4-oxoimidazo-[1,2-a]-quinoxaline-2-carboxylic acid, 0.15 mg of emulsifier and 50 mg of propellant.

PHARMACOLOGICAL ACTIVITY

Passive cutaneous anaphylaxis (PCA) in rats

Cutaneous anaphylaxis was induced in groups of 7 male rats weighing 180 to 220 grams by intradermal (ID) sensitization with antiserum followed, three days later, by systemic challenge with antigen. Evans blue dye injected with the antigen is used as a marker to assess the severity of the local response. Anti-allergic drugs inhibit this reaction and this method has been described by OVARY (1962) in "Passive Cutaneous Anaphylaxis in Allergology" 258–367 Ed. Brown; Pergamon Press.

Preparation of Antigen (or Sensitization) (Alum-precipitated ovalbumen)

1. Wash 120 grams of Al(OH)$_3$ gel in 140 ml of saline (use of a macerator facilitates mixing).
2. Centrifuge at 3,000 r.p.m. for about 10 minutes.
3. Resuspend the precipitate with 300 ml of albumen egg powder (1.3 mg/ml) in saline and allow to stand for 30 minutes.
4. Centrifuge at 3,000 r.p.m. for 10 minutes.
5. Weigh the wet precipitate and to each gram weight add 1 ml of saline. Store in frigerator.

(Quantity sufficient for 60 rats for a 3 day sensitization program).

Preparation of Antiserum (i.e. anti-ovalbumen)

1. 1 ml of the alum-precipitated ovalbumen was injected subcutaneously into 180–200 gram rats on days 0,2 and 4.
2. The rats were bled on day 14 either by cardiac puncture or via the dorsal abdominal aorta.
3. Equal quantities of serum from each animal were pooled and thoroughly mixed.

4. 2 ml of aliquots were stored at −20° C. in plastic tubes.

Serum dilution for PCA

The antiserum for sensitization was diluted so that an ID injection of 0.1 ml into control animals gave an average score of a single spot of between 2.0–3.5 using a 5 point scoring system (0,1,2,3,4)

METHOD (A) SENSITIZATION: Rats are anaesthetized with Nembutal (40–60 mg/kg i.p.) and then sensitized by four ID injections (0.1 ml each) on their shaved backs. The animals were then left for a period of three days to develop sensitization.

(B) CHALLENGE: The sensitized rats were anaesthetised and challenged orally or intravenously via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self filling glass syringe. The "challenged" rats were killed after 30 minutes, (usually pithed) and their skin on the dorsal surface was removed. The degree and area of blueing, proportional to the anaphylactic reaction, was assessed on a five point scoring system.

Calculations

1. Total scores for sites 1,2,3 and 4=X
2. Mean value of X for each group=$\bar{X}$
3. $\bar{X}$ t=$\bar{X}$ for test group; $\bar{X}$ c=$\bar{X}$ for control group
4. % inhibition=($\bar{X}$ c−$\bar{X}$ t)/$\bar{X}$ c×100/1
5. $ED_{50}$=dose of drug giving 50% inhibition $ED_{50}$ values for compounds tested in the passive cutaneous anaphylaxis screen (in rats):

| Compound of Example | $ED_{50}$ mg/kg I.V. | mg/kg P.O. |
|---|---|---|
| 2 | 0.16 | 2.0 |
| 4 | 0.031 | 1.28 |
| 5 |  | 0.16 |
| 6 | 0.01 | 0.45 |
| 8 | 0.01 | 0.24 |
| 10 | 0.023 | 0.59 |

Various modifications of the products and process of the invention may be made without departing from the spirit or scope thereof and it is to be understood that the invention is not intended to be limited only as defined in the appended claims.

We claim:

1. A compound selected from the group consisting of oximidazoquinoxalines of the formula

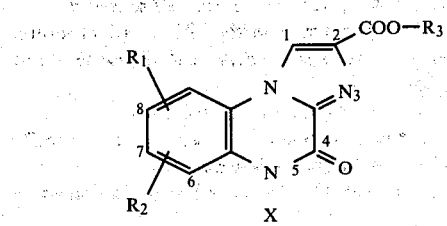

wherein $R_1$ and $R_2$ are individually selected from the group consisting of hydrogen, chlorine and bromine, X is selected from the group consisting of hydrogen, alkyl of 1 to 5 carbon atoms, cycloalkyl of 3 to 5 carbon atoms and cycloalkylalkyl of 4 to 6 carbon atoms, $R_3$ is selected from the group consisting of hydrogen, alkyl of 1 to 5 carbon atoms, alkali metal, alkaline earth metal, aluminum, —$NH_4$ and non-toxic, pharmaceutically acceptable organic amine and their non-toxic, pharmaceutically acceptable acid addition salts.

2. A compound of claim 1 wherein $R_3$ is selected from the group consisting of hydrogen and ethyl.

3. A compound of claim 1 wherein $R_1$ and $R_2$ are hydrogen and $R_3$ is selected from the group consisting of hydrogen and ethyl.

4. A compound of claim 1 selected from the group consisting of 4,5-dihydro-5-ethyl-4-oxoimidazo-[1,2-a]-quinoxaline-2-carboxylic acid, its alkali metal, alkaline earth metal, aluminum, —$NH_4$ and non-toxic, pharmaceutically acceptable organic amine salts and its non-toxic, pharmaceutically acceptable acid addition salts.

5. A compound of claim 1 selected from the group consisting of 4,5-dihydro-5-propyl-4-oxoimidazo-[1,2-a]-quinoxaline-2-carboxylic acid, its alkali metal, alkaline earth metal, aluminum, —$NH_4$ and non-toxic, pharmaceutically acceptable organic amines salts and its non-toxic, pharmaceutically acceptable acid addition salts.

6. An antiallergic composition comprising an antiallergically effective amount of a compound of claim 1 and an excipient.

7. A composition of claim 6 wherein $R_3$ is selected from the group consisting of hydrogen and ethyl.

8. A composition of claim 7 wherein $R_1$ and $R_2$ are hydrogen.

9. A composition of claim 6 wherein the compound is selected from the group consisting of 4,5-dihydro-5-ethyl-4-oxoimidazo-[1,2-a]-quinoxaline-2-carboxylic acid, its alkali metal, alkaline earth metal, aluminum, —$NH_4$ and non-toxic, pharmaceutically acceptable organic amine salts and its non-toxic, pharmaceutically acceptable acid addition salts.

10. A composition of claim 6 wherein the compound is selected from the group consisting of 4,5-dihydro-5-propyl-4-oxoimidazo-[1,2-a]-quinoxaline-2-carboxylic acid, its alkali metal, alkaline earth metal, aluminum, —$NH_4$ and non-toxic, pharmaceutically acceptable organic amine salts and its non-toxic, pharmaceutically acceptable acid addition salts.

11. A method of treating allergic symptoms in warm-blooded animals comprising administering to warm-blooded animals an antiallergically effective amount of a compound of claim 1.

12. The method of claim 11 wherein $R_3$ is selected from the group consisting of hydrogen and ethyl.

13. The method of claim 12 wherein $R_1$ and $R_2$ are hydrogen.

14. A method of claim 11 wherein the compound is selected from the group consisting of 4,5-dihydro-5-ethyl-4-oxoimidazo-[1,2-a]-quinoxaline-2-carboxylic acid, its alkali metal, alkaline earth metal, aluminum, —$NH_4$ and non-toxic, pharmaceutically acceptable organic amine salts and its non-toxic, pharmaceutically acceptable acid addition salts.

15. A method of claim 11 wherein the compound is selected from the group consisting of 4,5-dihydro-5-propyl-4-oxoimidazo-[1,2-a]-quinoxaline-2-carboxylic acid, its alkali metal, alkaline earth metal, aluminum, —$NH_4$ and non-toxic, pharmaceutically acceptable organic amine salts and its non-toxic, pharmaceutically acceptable acid addition salts.

* * * * *